US011046584B2

(12) United States Patent
Atkins et al.

(10) Patent No.: US 11,046,584 B2
(45) Date of Patent: *Jun. 29, 2021

(54) METHODS FOR PRODUCING ADVANCED CARBON MATERIALS FROM COAL

(71) Applicant: CARBON HOLDINGS INTELLECTUAL PROPERTIES, LLC, Sheridan, WY (US)

(72) Inventors: Charles Agee Atkins, Sheridan, WY (US); Garrett W. Lindemann, Buffalo, WY (US); Matthew Targett, Sheridan, WY (US)

(73) Assignee: Carbon Holdings Intellectual Properties, LLC, Sheridan, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,695

(22) Filed: Dec. 21, 2018

(65) Prior Publication Data

US 2019/0194544 A1   Jun. 27, 2019

Related U.S. Application Data

(60) Provisional application No. 62/610,037, filed on Dec. 22, 2017.

(51) Int. Cl.
*C01B 32/336* (2017.01)
*C01B 32/184* (2017.01)
(Continued)

(52) U.S. Cl.
CPC ............ *C01B 32/336* (2017.08); *C01B 3/02* (2013.01); *C01B 32/05* (2017.08); *C01B 32/154* (2017.08);
(Continued)

(58) Field of Classification Search
CPC ..... C01B 32/05; C01B 32/154; C01B 32/158; C01B 32/16; C01B 32/182; C01B 32/184;
(Continued)

(56) References Cited

U.S. PATENT DOCUMENTS 2,624,698 A * 1/1953 Hickey .................. C01B 32/00
423/461
3,639,953 A 2/1972 Kimura et al.
(Continued)

FOREIGN PATENT DOCUMENTS

CN   105836739 A   8/2016

OTHER PUBLICATIONS

Black, Sara, Coal as an avenue to low-cost carbon fibers, Oct. 18, 2017, Composite World; https://www.compositesworld.com/articles/coal-as-an-avenue-to-low-cost-carbon-fibers (Year: 2017).*
(Continued)

*Primary Examiner* — Cephia D Toomer
(74) *Attorney, Agent, or Firm* — Dorsey & Whitney LLP

(57) ABSTRACT

A method of producing advanced carbon materials can include providing coal to a processing facility, beneficiating the coal to remove impurities from the coal, processing the beneficiated coal to produce a pitch, and treating the pitch to produce an advanced carbon material such as carbon fibers, carbon nanotubes, graphene, resins, polymers, biomaterials, or other carbon materials.

17 Claims, 9 Drawing Sheets

(51) Int. Cl.
| | |
|---|---|
| C01B 3/02 | (2006.01) |
| G01N 33/22 | (2006.01) |
| C10C 3/00 | (2006.01) |
| D01F 9/12 | (2006.01) |
| C01B 32/50 | (2017.01) |
| C01B 32/30 | (2017.01) |
| C01B 32/20 | (2017.01) |
| C01B 32/182 | (2017.01) |
| C01B 32/158 | (2017.01) |
| C10B 53/04 | (2006.01) |
| C01B 32/205 | (2017.01) |
| C01B 32/05 | (2017.01) |
| C01B 32/154 | (2017.01) |
| C01B 32/16 | (2017.01) |
| C08F 6/28 | (2006.01) |
| C10B 53/00 | (2006.01) |
| C10B 57/08 | (2006.01) |
| D01F 9/15 | (2006.01) |
| C08F 10/02 | (2006.01) |
| C08F 10/06 | (2006.01) |
| C08F 20/44 | (2006.01) |
| C10G 1/00 | (2006.01) |
| C10G 1/02 | (2006.01) |
| C10G 1/04 | (2006.01) |
| C10G 17/02 | (2006.01) |
| C10G 27/12 | (2006.01) |

(52) U.S. Cl.
CPC ............ *C01B 32/158* (2017.08); *C01B 32/16* (2017.08); *C01B 32/182* (2017.08); *C01B 32/184* (2017.08); *C01B 32/20* (2017.08); *C01B 32/205* (2017.08); *C01B 32/30* (2017.08); *C01B 32/50* (2017.08); *C08F 6/28* (2013.01); *C08F 10/02* (2013.01); *C08F 10/06* (2013.01); *C08F 20/44* (2013.01); *C10B 53/00* (2013.01); *C10B 53/04* (2013.01); *C10B 57/08* (2013.01); *C10C 3/00* (2013.01); *C10C 3/002* (2013.01); *C10G 1/002* (2013.01); *C10G 1/02* (2013.01); *C10G 1/04* (2013.01); *D01F 9/12* (2013.01); *D01F 9/15* (2013.01); *G01N 33/222* (2013.01); *C10G 17/02* (2013.01); *C10G 27/12* (2013.01); *D10B 2101/12* (2013.01)

(58) Field of Classification Search
CPC ....... C01B 32/20; C01B 32/205; C01B 32/30; C01B 32/336; C01B 32/50; C01B 3/02; C08F 10/02; C08F 10/06; C08F 20/44; C08F 6/28; C10C 3/00; C10C 3/002; C10G 17/02; C10G 1/002; C10G 1/02; C10G 1/04; C10G 27/12; D01F 9/12; D01F 9/15; C10B 53/00; C10B 53/04; C10B 57/08; D10B 2101/12
See application file for complete search history.

(56) References Cited

U.S. PATENT DOCUMENTS

| | | |
|---|---|---|
| 4,439,304 A | 3/1984 | Sudbury et al. |
| 4,701,838 A | 10/1987 | Swinkels et al. |
| 4,804,390 A | 2/1989 | Lloyd et al. |
| 5,403,365 A | 4/1995 | Merriam et al. |
| 5,692,807 A | 12/1997 | Zimmerman |
| 6,771,368 B1 | 8/2004 | Chadwick |
| 7,078,008 B2 | 7/2006 | Allison et al. |
| 7,842,644 B2 | 11/2010 | Kai et al. |
| 8,148,435 B2 | 4/2012 | Fiato |
| 9,068,123 B2 | 6/2015 | Kramer et al. |
| 9,074,138 B2 | 7/2015 | Rinker |
| 9,181,509 B2 | 11/2015 | Bland et al. |
| 10,144,874 B2 | 12/2018 | Walter et al. |
| 2009/0061193 A1 | 3/2009 | Hara et al. |
| 2011/0011719 A1 | 1/2011 | Rinker |
| 2012/0076703 A1 | 3/2012 | Stiller et al. |
| 2014/0120030 A1 | 5/2014 | Kim et al. |
| 2014/0223882 A1 | 8/2014 | Shah et al. |
| 2015/0141726 A1 | 5/2015 | Thakkar et al. |
| 2016/0060122 A1 | 3/2016 | Tour et al. |
| 2017/0080399 A1 | 3/2017 | Johnson et al. |
| 2017/0198221 A1 | 7/2017 | Targett et al. |
| 2017/0313886 A1 | 11/2017 | Colyar et al. |
| 2018/0155201 A1 | 6/2018 | Zhang |
| 2019/0194022 A1 | 6/2019 | Atkins et al. |
| 2019/0194025 A1 | 6/2019 | Atkins et al. |
| 2019/0194364 A1 | 6/2019 | Atkins et al. |
| 2019/0194828 A1 | 6/2019 | Atkins et al. |

OTHER PUBLICATIONS

Andresen, John M., et al. "Synthesis of pitch materials from hydrogenation of anthracite." Fuel processing technology 85.12 (2004): 1361-1372.

Li, Gang, et al. "One-step green synthesis of nitrogen and phosphorus co-doped pitch-based porous graphene-like carbon for supercapacitors." Journal of Porous Materials 24.6 (2017): 1689-1696.

IUPAC. Compendium of Chemical Terminology, 2nd ed. (the "Gold Book"). Compiled by A. D. McNaught and A. Wilkinson. Blackwell Scientific Publications, Oxford (1997)., Online version (2019-) created by S. J. Chalk. ISBN 0-9678550-9-8. https://doi.org/10.1351/goldbook.

Ye, Ruquan et al., "Bandgap engineering of coal-derived graphene quantum dots. (Supporting Information)" ASC applied materials & interfaces 7.12 (2015): S1-S5.

International Search Report and Written Opinion for PCT Application No. PCT/US2018/067341, dated May 23, 2019.

International Search Report and Written Opinion for PCT Application No. PCT/US2018/067351, dated May 2, 2019.

Kim, et al., "Pitch-Based Carbon Fibers From Coal Tar or Petroleum Residue Under the Same Processing Condition", Carbon Letters vol. 19, Jun. 14, 2016, 72-78.

International Preliminary Report on Patentability received for International Application No. PCT/IB2018/067351, dated Jul. 2, 2020, 10 pages.

International Preliminary Report on Patentability Received for International Application No. PCT/US2018/067341, dated Jul. 2, 2020, 10 pages.

* cited by examiner

METHODS FOR PRODUCING ADVANCED CARBON MATERIALS FROM COAL

CROSS-REFERENCE TO RELATED APPLICATIONS

The present application claims the benefit of U.S. Provisional Patent Application No. 62/610,037 filed on 22 Dec. 2017, titled "Methods for Producing Advanced Carbon Materials from Coal," the disclosure of which is incorporated herein, by reference, in its entirety.

BACKGROUND

Coal is a highly varied heterogeneous material that has been mined and principally used for three purposes over thousands of years: 1) the generation of thermal heat and power generation through incineration, 2) the production of steel and other metals by coking, and 3) the production of what are now widely known as "petrochemicals" through pyrolysis or liquefaction. Despite the fact that coal has been extensively used for thousands of years, more than 99% of it has been incinerated to produce heat and power. This process is now widely known to produce a host of adverse environmental and economic effects.

Additional uses of coal has been the topic of research for many years. The basic chemistry of coal was well understood by at least the early twentieth century. Significant research was conducted with the aim of deriving liquid transportation fuels from coal in order to supplant petroleum. One notable breakthrough was the development of the Fischer-Tropsch process in Germany, around 1925, which converted gasified coal into liquid hydrocarbons. Additionally, Sasol, a major South African company, focused on the conversion of solid coal to liquid transportation fuels via catalytic cracking. Similarly, the United States Department of Energy sought to develop coal-based transportation fuels as an alternative to petroleum-based fuels. However, due to research driven petroleum technology and the decreasing costs of petroleum, the use of coal to produce liquid transportation fuels at large scales never became economically feasible.

Throughout history, numerous other products have been derived from coal. For example, many novel and high-value byproducts have been identified and developed from the feedstock as well as from the byproducts generated from the modification and combustion of coal, as well as the extraction of carbon from coal. These second, third, and fourth generation coal products and byproducts can be more valuable than the input natural resource as ingredients in the manufacture of shingles, asphalt, mascara, printer ink, organic oils, organic solvents, fuel, water filters, air filters, and dialysis filters. Further, coal derived products have usage in agriculture, pharmaceuticals, chemicals, healthcare, cosmetics, construction, and nearly every other existing industry.

Activated carbon can also be formed from coal and can be used to produce specialized high value filter components. Activated carbon is not limited to being components of filters, it can also be used for treatments including poisonings and overdoses; diarrhea, indigestion, and flatulence; chromatographic stationary and mobile phases for analytical chemistry; hazardous materials remediation; and agricultural usages including as a pesticide, disinfectant, and as an animal feed additive.

Although significant research has been conducted on coal liquefaction and the use of coal to form other products for more than a century, the focus has long been on increasing the hydrogen to carbon ratio of coal in order to form these products. In contrast, the ability to produce carbon based products that have a lower hydrogen to carbon ratio than the initial coal remains an open question. In recent years, carbon-based technologies have come to the forefront, with rapid developments being made in in the commercialization of advanced carbon materials such as carbon fiber, graphene, and carbon nanotubes, materials with extremely low hydrogen to carbon ratios. As these advanced materials are increasingly used in mass produced, high volume applications, there is a need to quickly and economically supply large quantities of advanced carbon materials to manufacturers. Thus, while improvements in the derivation of fuels and other products from coal are being explored, there remains significant work to be done in developing processes to reduce the hydrogen to carbon ratio of coal and convert coal into the advanced carbon materials that include new and different material properties and characteristics and that will be instrumental in the economy of the future.

SUMMARY

A method of producing an advanced carbon material includes providing an amount of coal to a processing facility, beneficiating the amount of coal at the processing facility to remove impurities therefrom, processing the beneficiated amount of coal at the processing facility to produce an amount of pitch from at least some of the amount of coal, and treating at least some of the amount of pitch at the processing facility to produce the advanced carbon material.

The method of producing an advanced carbon material can include providing coal to a processing facility by extracting coal from a coal mine.

The method of producing an advanced carbon material can include providing coal to a processing facility by extracting coal from the coal mine via a high wall coal mining process.

The method of producing an advanced carbon material can include transporting coal extracted from the coal mine to the processing facility.

The method of producing an advanced carbon material can include using raw coal as an initial material.

The method of producing an advanced carbon material can include heating the amount of coal to a first temperature for a first duration, and heating the amount of coal to a second, higher temperature for a second duration.

The method of producing an advanced carbon material can include removing impurities from the coal, such as mercury. Beneficiating the coal can remove at least 85% of mercury from the coal.

The method of producing an advanced carbon material can include removing water from the coal.

The method of producing an advanced carbon material can include beneficiating the coal to produce a beneficiated amount of coal having less than about 5 wt. % of water.

The method of producing an advanced carbon material can include removing volatile matter from the coal. Removal of at least 50% of the volatile matter can be removed from the coal.

The method of producing an advanced carbon material can include processing the beneficiated amount of coal at the processing facility to produce an amount of pitch from at least some of the amount of coal, including subjecting the beneficiated amount of coal to a pyrolysis process.

The method of producing an advanced carbon material can include processing the beneficiated amount of coal at the processing facility to produce an amount of pitch from at least some of the amount of coal, including subjecting the beneficiated amount of coal to a direct liquefaction process.

The method of producing an advanced carbon material can include processing the beneficiated amount of coal at the processing facility includes subjecting the beneficiated amount of coal to an indirect liquefaction process.

The method of producing an advanced carbon material can include processing the beneficiated amount of coal at the processing facility includes producing an amount of solid char.

The method of producing an advanced carbon material can include treating at least some solid char to produce an amount of activated carbon.

The method of producing an advanced carbon material can include processing the beneficiated amount of coal at the processing facility includes producing an amount of coal liquid extract.

The method of producing an advanced carbon material can include treating at least some of the coal liquid extract to produce an amount of benzene.

The method of producing an advanced carbon material can include treating at least some of the coal liquid extract to produce an amount of paraxylene.

The method of producing an advanced carbon material can include using pitch that comprises one of mesophase pitch, isotropic pitch, or mesophase pitch.

The method of producing an advanced carbon material can include spinning at least some of the amount of pitch to produce the advanced carbon material.

The method of producing an advanced carbon material can include forming advanced carbon materials including one or more of carbon fibers, carbon nanotubes, graphite, graphene, graphite nano-platelets, fullerenes, pyrolytic carbon, carbon foams, and resins.

The method of producing an advanced carbon material can include treating at least some of the amount of pitch at the processing facility including treating a first amount of pitch to form a first advanced carbon material and treating a second amount of pitch to form a second advanced carbon material.

The method of producing an advanced carbon material wherein the first advanced carbon material includes carbon fibers and the second advanced carbon material includes a polymer.

The method of producing an advanced carbon material can include combining the carbon fibers and the polymer to form a carbon fiber reinforced polymer.

According to some embodiments, a method of producing synthetic graphite from coal at a processing facility, can comprise providing coal to the processing facility, beneficiating the coal to remove a desired amount or range of amounts of impurities therefrom, and processing the beneficiated coal to produce synthetic graphite.

The synthetic graphite includes a desired amount or range of amounts of impurities. The impurities can include one or more of cadmium, selenium, or other metals. The method can further comprise processing the synthetic graphite to produce synthetic graphene. Processing the synthetic graphite to produce synthetic graphene can comprise exfoliation. The synthetic graphene can include a desired amount or range of amounts of impurities.

According to some embodiments, a synthetic graphite formed from pitch derived from coal is described herein. The synthetic graphite can further comprise a desired amount or range of amounts of one or more impurities found in coal.

According to some embodiments, a synthetic graphene formed from pitch derived from coal is described herein. The synthetic graphene can further comprise a desired amount or range of amounts of one or more impurities found in coal.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
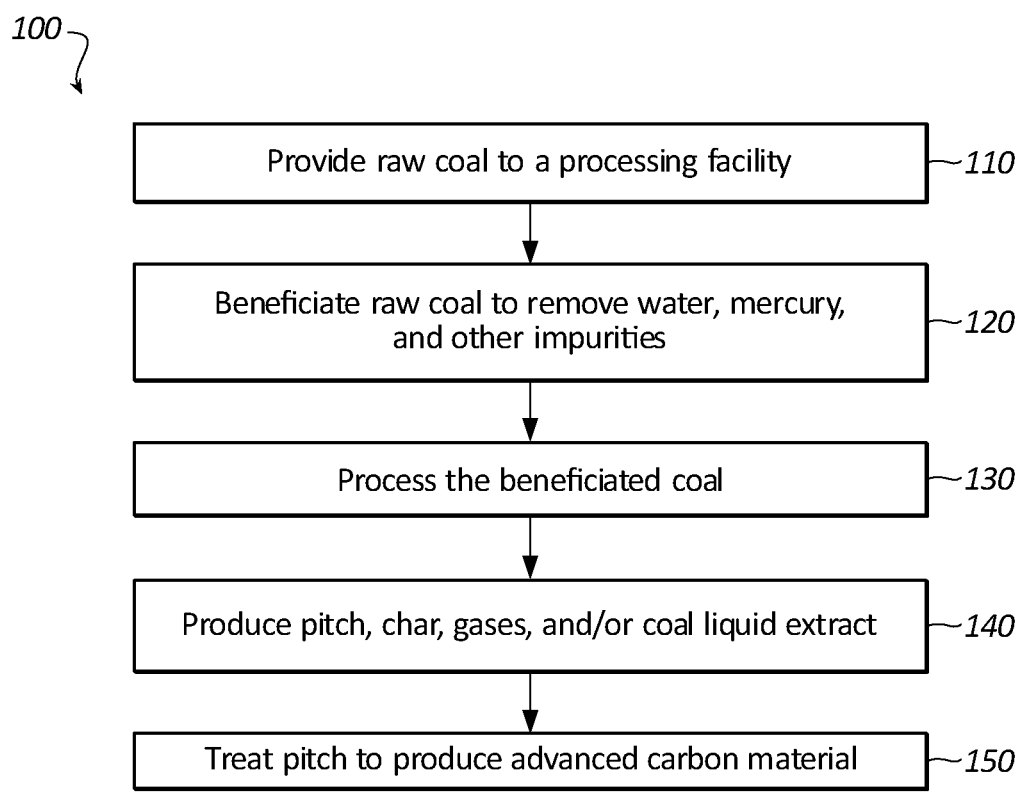
FIG. 1 illustrates a process flow diagram of an example of a method of producing advanced carbon materials from coal in accordance with the present disclosure.

Although significant research has been conducted on coal liquefaction and the use of coal to form other products for more than a century, the focus has long been on increasing the hydrogen to carbon ratio of coal, in order to form these products. In contrast, the ability to produce carbon based products that have a lower hydrogen to carbon ratio than the initial coal remains an open question. In recent years, carbon-based technologies have come to the forefront, with rapid developments being made in in the commercialization of advanced carbon materials such as carbon fiber, graphene, and carbon nanotubes, materials with extremely low hydrogen to carbon ratios. As these advanced materials are increasingly used in mass produced, high volume applications, there is a need to quickly and economically supply large quantities of advanced carbon materials to manufacturers.

As described below, advanced carbon materials can be produced from raw, mined coal. In some embodiments, raw coal can be transported to a processing facility which can then produce advanced carbon materials therefrom. The coal can then be beneficiated in order to remove a desired amount or range of amounts of impurities, for example mercury, arsenic, cadmium, other heavy metals, water, and volatile compounds. In some cases, beneficiating can decrease the hydrogen to carbon (H:C) ratio of the coal. In some cases, beneficiation can include heating the coal to remove these impurities. The beneficiated coal can then be processed to produce a pitch, activated carbon, and/or other precursors or advanced carbon materials. The processing can include subjecting the beneficiated coal to a pyrolysis process, direct liquefaction process, indirect liquefaction process, or processing involving one or more membranes. In some cases, these processes can produce byproducts, such as gases, solid char, and coal liquid extract which themselves can be processed to form useful materials, such as other advanced carbon materials. For example, solid char can be processed to form activated carbon, and coal liquid extract can be processed to form aromatic compounds such as benzene and paraxylene, or pitch. The processed coal liquid extract, for example in the form of aromatics or pitch, can be subjected to further processing to form advanced carbon materials such as carbon fibers, graphene, resins, and the like.

In some cases, processing the coal, for example the beneficiated coal can result in a pitch, resin, advanced carbon material, and/or advanced carbon material precursor that has a H:C ratio lower than an H:C ratio of the raw coal prior to processing. For example, raw coal can have an H:C ratio of from about 1 to about 0.6, in some cases about 0.8. After being subjected to a method as described herein, the resultant advanced carbon material or precursor can have a hydrogen to carbon ratio of less than about 0.5, less than about 0.2, or less than about 0.1. The low hydrogen to carbon ratio achieved by beneficiation and/or other processes described herein can improve the yield of resin, pitch, or other products formed from the coal, can eliminate the need for an external source of hydrogen during one or more processing steps, and/or reduce the amount of carbon dioxide produced during the processes disclosed herein.

As used herein, the term resin or resin products can be used to refer to resinous material as well as pitch, tar, and asphalt. In some cases, the term resin can be used to refer to a material that does not include a long polymeric chain, but can instead include, for example, fused aromatic ring structures, such as polycyclic aromatic hydrocarbons (PAH). In some cases, the term resin can be used herein to refer to both PAHs and conventional petro-chemically derived polymers.

In some embodiments, the pitch or materials produced by the processes described herein can be an isotropic pitch, and can be converted to a mesophase pitch by processing as needed or desired. The pitch can then be treated to produce one or more advanced carbon materials. For example, the pitch can be spun to form carbon fibers. In some cases, the pitch can be processed to form synthetic graphite, which can be subjected to further processing to form or produce synthetic graphene having one or more desired physical, chemical, and/or electrical properties. These advanced carbon materials can be subjected to further processing, or can be delivered to third parties for use, for example in manufacturing. In some cases one or more advanced carbon materials can be produced and combined to form secondary material, such as a carbon reinforced polymer.

In some cases, processing the coal can include forming or producing pitch, for example in the form of isotropic pitch, and subjecting the pitch to further processing to produce a mesophase pitch. For example, an product or precursor, such as isotropic pitch, can be heated to a temperature of from about 300° C. to about 500° C., from about 350° C. to about 450° C., or from about 380° C. to about 440° C. In some cases, the product or precursor can be heated in an inert atmosphere, for example an atmosphere containing a noble gas such as argon. In some cases, the product or precursor can be heated in an atmosphere that does not include $H_2$. In some cases, the product or precursor can be agitated, stirred, sonicated, and/or subjected to a treatment to produce an emulsion before, during, and/or after being heated.

In some embodiments, one or more gases can be generated or produced during beneficiation, pitch production, and/or other processing steps as described herein. In some cases, these gases can be captured or otherwise contained and/or used during the processes described herein. The gases captured during certain process steps can be used in subsequent process steps, for example in the production or refinement of advanced carbon materials as described herein. In some cases, gases produced by and a captured as part of the processes described herein can be utilized by these same or subsequent processes in order to increase the efficiency and/or cost effectiveness of said processes. In some cases, these gases can be used as in the formation of advanced carbon materials as described herein, for example as precursors to advanced carbon materials. Thus, in some cases, gases produced by coal as described herein can be used to form advanced carbon materials. In some embodiments, the captured gas or gases can comprise hydrogen and/or carbon. In some cases, the captured gas or gases can comprise sulfur. Such gases can include, for example, $H_2$, $CO_2$, CO, $CH_4$, $C_2H_4$, $C_3H_6$, and/or other hydrocarbon gases.

In some embodiments, one or more of the processes or process steps described herein can utilize or be carried out in the presence of one or more catalysts. For example, one or more process can include a hydrogenation catalyst. In some embodiments, the catalyst can comprise a metal, for example platinum. In some cases, the catalyst can be a multi-part catalyst, for example a catalyst comprising two or more metals. In some cases, a catalyst can include a ceramic or mineral material, for example a silicate material, such as an aluminosilicate material. In some cases, a catalyst can include any catalytic material now known or as can yet be discovered for use in processing coal.

In some embodiments, all of the beneficiation, processing, and treatment steps described herein can be performed at a single processing facility, for example a single processing plant or compound. However, in other embodiments, one or more steps can be performed at separate facilities and the products of each step can be stored and transported between each facility. As used herein, the term processing facility can refer to one or more laboratories, buildings, process flows, or other apparatuses at about the same geographic location. For example, a processing facility can comprise a single building or factory complex at a single geographic location which comprises such equipment to perform the processes and methods described herein.

The advanced carbon materials which can be produced by the processes described herein can include, but are not limited to, carbon fibers, carbon foams, single-walled carbon nanotubes, multi-walled carbon nanotubes, carbon megatubes, graphite, graphene, graphite nano-platelets, nanoribbons, nanobuds, fullerenes, such as buckminsterfullerene and multi-cored fullerenes, quantum dots, activated carbon, and pyrolyzed carbon. The advanced carbon materials produced by the processes described herein can also include, but are not limited to resins and polymers, such as polyacrylonitrile, polyurethane resins, cyanate ester resins, epoxy resins, methacrylate resins, polyester resins, and others. The advanced carbon materials produced by the processes described herein can also include materials that can be used as precursors in the formation of other advanced carbon materials. In some cases, these advanced carbon materials can include alkanes, alkenes, and/or alkynes. In some cases, advanced carbon materials can comprise biologically useful materials or biopolymers, such as proteins, amino acids, nucleic acids, collagen, chitosan, and/or sugars.

In some embodiments, coal can be provided by any method that is now known or that can be developed in the future. For example, coal is generally extracted from naturally occurring layers or veins, known as coal beds or coal seams, by mining. Coal can be extracted by surface mining, underground mining, or various other forms of mining. Typically, coal that has been extracted via mining, but has not been otherwise processed is referred to as raw coal. In some embodiments, raw coal can be provided to a processing facility and used to produce advanced carbon materials as described herein. In some cases, the raw coal can be extracted via a surface mining process, such as a high wall mining process, strip mining process, or contour mining process. In some cases, the raw coal can be extracted via an underground mining process, such as by a longwall mining process, continuous mining process, blast mining process, retreat mining process, or room and pillar mining process.

The raw coal can be mined or extracted from a location relatively near to the processing facility. For example, the processing facility can be located at, or near a coal extraction area. However, in other cases coal can be extracted from any location and transported to the processing facility. In some cases raw coal can be provided to the processing facility as needed to produce a desired amount of advanced carbon materials. However, in some other cases, raw coal can be provided and stored at the processing facility until it is processed.

Coal can be ranked or graded based on its contents and properties. Although a variety of coal classification schemes exist, a general metamorphic grade is used herein to generally describe raw coal. These grades are used generally to aid in the understanding of the present disclosure and are not intended to limit to types of coal which can be used to produce advanced carbon materials as described herein. While certain classifications of coal can be preferable for use in the processes described herein, such processes are not strictly limited to the discussed classifications of coal, if any. In some embodiments, the coal utilized by the processes described herein can be lignite coal, and can have a volatile content of greater than about 45 wt. %. In some embodiments, the coal can be sub-bituminous coal, bituminous coal, and/or anthracite coal. In some embodiments, the coal can be coal extracted from the Brook Mine near Sheridan, Wyo. In some cases, the preferred coal for use in the processes described herein can be selected by the skilled artisan. According to some embodiments, and as illustrated in FIG. 1, an advanced carbon material can be produced from coal by a method or process 100 including:

providing coal to a processing facility at block 110;

beneficiating the coal via the processing facility at block 120 to remove a desired amount or range of amounts of water, metals, and/or other impurities from the coal;

processing at least some of the beneficiated coal via the processing facility at block 130;

producing pitch, char, gases, and/or coal liquid extract at block 140; and treating the pitch via the processing facility at block 150 to produce the advanced carbon material.

Although the method 100 describes a process flow for producing a single type of advanced carbon material via a processing facility, the method 100 can be used to produce more than one type of advanced carbon material via the processing facility. For example, the method 100 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 100. Further, while producing pitch, char, and/or coal liquid extract is described as a separate block 140, the pitch, char, and/or coal liquid extract can be produced as a result of blocks 120 and/or 130 and may not be a separate process step in and of itself.

As described herein, raw coal can be provided to a processing facility at block 110 for use in the method 100. The processing facility can have the capacity to store raw coal for use as needed, or can receive raw coal as needed to produce a desired amount of advanced carbon material. As is well known in the art, coal can be provided via truck, train, or any other form of transportation. Further, the processing facility can be situated at a coal extraction site, such that coal extraction site can be considered as part of the processing facility.

At block 120, the raw coal can be beneficiated to remove contaminants or impurities such as water, heavy metals, and/or volatile compounds from the raw coal, thereby producing beneficiated or upgraded coal. In some cases, the beneficiation process can comprise heating the raw coal to a desired temperature for a first duration. In some embodiments, beneficiation can also include heating the raw coal to a second, higher desired temperature of a second duration. In some embodiments, the coal can be heated in an atmosphere comprising a halogen gas. In some embodiments, beneficiation can include subjecting the raw coal to a WRITECoal beneficiation process, as described, for example, in U.S. Pat. No. 9,181,509 which is hereby incorporate by reference in its entirety. In some other embodiments, the coal can be beneficiated by heating the coal to a desired temperature in the presence of one or more catalyst compounds. In some cases, beneficiating the coal can comprise pyrolyzing the coal, for example in the presence of a catalyst. In some cases, the coal can be beneficiated by the BenePlus System, as developed and licensed by LPAmina and as described, for example, in U.S. Patent Publication No. 2017/0198221 which is hereby incorporated by reference in its entirety.

In some cases, beneficiation can comprise heating an amount of coal to one or more temperatures for a desired duration. For example, beneficiation can include heating an amount of coal to between about 100° C. and about 150° C. In some cases, this heating can be carried out at about atmospheric pressure. In some cases, such a heating profile can remove a desired amount or range of amounts of moisture from the coal. In some cases, beneficiation can comprise heating an amount of coal to one or more temperatures for a desired duration. For example, beneficiation can include heating an amount of coal to between about 150° C. and about 290° C. In some cases, this heating can be carried out at about atmospheric pressure. In some cases, such a heating profile can remove a desired amount or range of amounts of one or more impurities or contaminants from the coal.

The beneficiated coal can comprise a significantly reduced amount of mercury, cadmium, other heavy metals, water, and/or other impurities. As used herein, an impurity can be considered any element or compound other than carbon or hydrogen. For example, beneficiating the coal can reduce the amount of mercury in the coal by about at least about 70%, 75%, 80%, 85%, 90%, or 92% or more. In some cases, beneficiating the coal can reduce the water or moisture content of the coal to less than about 5 wt. %, 4 wt. %, 3 wt. %, 2 wt. %, 1.5 wt. %, 1.45 wt. %, 1.4 wt. %, or lower. In some cases, beneficiating the coal can remove one or more of hydrogen, sulfur, oxygen, arsenic, selenium, cadmium, or volatile matter from the coal. The amount of one or more of these elements in the coal can be reduced by from about 25% to about 90%. Additionally, the beneficiated coal can have a reduced H:C ratio as compared to the raw or beneficiated coal. For example, the beneficiation process at block 150 can reduce the amount of hydrogen in the coal. In some cases, a H:C ratio of the beneficiated coal can be less than about 0.6, less than about 0.5, less than about 0.4, less than about 0.3, less than about 0.2, or less than about 0.1 or lower.

However, in some cases it can be desirable for a desired amount or range of amounts of one or more impurities to remain in the beneficiated coal after being subjected to a beneficiation process. For example, in some embodiments a beneficiation process can remove a desired amount or range of amounts of impurities such that a predetermined amount of cadmium, selenium, or other elements such as boron, or nitrogen can remain in the beneficiated coal after processing. In some cases, the desired amount or range of amounts of impurity that can remain in the coal after beneficiation can be useful in the subsequent formation of advanced carbon materials, and/or can be incorporated into the advanced carbon materials. For example, in some embodiments where the advanced carbon material comprises synthetic graphene, a desired amount or range of amounts of cadmium, gold, and/or silver can remain in the beneficiated coal and can be incorporated into the synthetic graphene to thereby improve the electrical, mechanical, or chemical properties thereof.

In some embodiments, beneficiating the coal can produce various other products that can be captured and used in later processing steps, that can be valuable in and of themselves, or that can be subjected to further processing or use in the method 100. That is, in some embodiments, beneficiating the coal can produce or separate gases or liquids from the raw coal. These gases and/or liquids can be captured or separated during processing. For example, beneficiating the coal at block 120 can produce $H_2$, $CO_2$, $CO$, $CH_4$, $C_2H_4$, $C_3H_6$, and/or other hydrocarbon gases, which can be captured and subsequently utilized in block 130 or in other process steps. In some cases, beneficiating the coal can result in liquids such as C2, C3, and/or C4 hydrocarbons, toluene, and/or benzene which can be captured for subsequent use or processing. In some cases, the impurities removed from the coal by the beneficiation process at block 120 can be captured for subsequent use. For example, water removed from the coal by the beneficiation process can be capture and utilized in subsequent process steps. In some embodiments, beneficiating the coal can also produce a solid material known as ash or char. In some cases, this char can be subjected to further processing to form activated carbon.

At block 130 the beneficiated coal, also referred to as upgraded coal, can be processed via the processing facility. In some embodiments, processing the beneficiated coal can include subjecting the upgraded coal to a liquid extraction process, such as a pyrolysis process, a direct liquefaction process, an indirect liquefaction process, or a process including one or more membranes.

In some embodiments, block 130 can comprise pyrolyzing the beneficiated coal via the processing facility. In some embodiments pyrolyzing the beneficiated coal can comprise heating the coal above a desired temperature for a duration. In some cases, the coal can be heated at high pressure and in the presence of a solvent. For example, the upgraded coal can be pyrolyzed in the presence of a $CO_2$ solvent which can be held in a supercritical state. In some cases, the upgraded coal can be pyrolyzed by the MuSCL System developed by TerraPower as described, for example, in U.S. Pat. No. 10,144,874 which is hereby incorporate by reference in its entirety.

In some cases, block 130 can include a pyrolysis process that includes heating the beneficiated coal to a temperature or temperatures between about 400° C. and about 650° C. for a duration. In some cases, the pyrolysis process can be carried about at or near atmospheric pressure. In some cases, block 130 can additionally or alternatively include a pyrolysis process that includes heating the beneficiated coal to a temperature up to about 1000° C.

In some embodiments, the pyrolysis process can comprise exposing the upgraded coal to electromagnetic radiation at a desired intensity and for a desired duration. For example, block 130 can comprise exposing the upgraded coal to microwave and/or radiofrequency (RF) radiation for a desired duration as part of the pyrolysis process. In some cases, this pyrolysis process can result in the bulk of the upgraded coal remaining below pyrolytic temperatures, while individual particles of coal can be subjected to temperatures greater than about 1200° F. In some cases, this pyrolysis process can also comprise methane activation and/or methylation of at least some of the carbon comprising the upgraded coal. In some embodiments, the upgraded coal can be pyrolyzed by the Wave Liquefaction process developed by H Quest Vanguard, Inc. as described, for example, in U.S. Patent Publication No. 2017/0080399 which is hereby incorporate by reference in its entirety.

In some embodiments, block 130 can comprise subjecting the upgraded coal of block 120 to a liquefaction process. In some embodiments, the liquefaction process can be a direct liquefaction process. In some other embodiments, the liquefaction process can be an indirect liquefaction process.

In some cases where block 130 comprises a direct liquefaction process, the upgraded coal can be heated above a desired temperature for a duration. In some cases, the upgraded coal can be heated in the presence of one or more catalysts and/or at an elevated pressure. In some cases, the upgraded coal can be heated in an atmosphere comprising $H_2$. In some cases, the direct liquefaction process can be a hydrogenation or hydro-cracking process. In some cases, the upgraded coal can be subjected to a direct liquefaction process developed by Axens as described, for example, in U.S. Patent Publication No. 2017/0313886 which is hereby incorporated by reference in its entirety.

In some cases, a direct liquefaction process can include heating the beneficiated coal to a temperature or temperatures between about 400° C. and about 500° C. for a duration. In some cases the beneficiated coal can be heated under pressure, for example the heated coal can be subjected to a pressure between about 10 bar and about 1000 bar. Further, as described herein, in some cases the coal can be heated in the presence of one or more solvents, or in the presence of $H_2$ gas.

In some embodiments, block 130 can comprise an indirect liquefaction process, where the upgraded coal can be converted to a gas or gases, which can then be converted to one or more liquids. For example, an indirect liquefaction process can include heating the upgraded coal to a desired temperature for a desired duration at a desire pressure, such as an elevated pressure. In some cases, this can convert at least some of the upgraded coal to a gas or gases, such as syngas, a mixture of $H_2$ and CO gas. In some cases, these gases, such as syngas, can then be converted to liquids or other materials. For example, the syngas can be converted to ammonia or methanol, which can in turn be subjected to further processing to produce hydrocarbons. In some cases, the gases can be processed to ultimately produce olefins, such as ethylene and propylene. In some cases, the gases can be processed to produce hydrocarbons, such as aromatic hydrocarbons. In some cases, the gases can be processed to produce hydrocarbons such as toluene, benzene, paraxylene, or other hydrocarbons, such as C2, C3, and/or C4 hydrocarbons, or polymers and resins. In some cases, the gases can be converted to olefins by a process developed by Honeywell UOP as described, for example, in U.S. Patent Publication No. 2015/0141726 which is hereby incorporated by reference in its entirety. In some cases, the upgraded coal can be subjected to an indirect liquefaction process.

In some cases, an indirect liquefaction process can comprise heating the beneficiated coal to a temperature or temperatures between about 250° C. and about 350° C. for a duration. In some cases this heating can occur under elevated pressure, for example between about 10 bar and about 40 bar of pressure. In some cases, an indirect liquefaction process can comprise heating the beneficiated coal to a temperature or temperatures between about 1400° C. and about 1600° C. for a duration. In some cases this heating can occur under elevated pressure, for example between about 40 bar and about 60 bar of pressure.

In some embodiments, block 130 can comprise processing the beneficiated coal in the presence of one or more membranes. In some cases, these membranes can serve to physically and/or chemically separate and/or crack the beneficiated coal to produce products therefrom. In some cases, a membrane can be a hydrogen selective membrane. In some cases, the membrane or membranes can include a ceramic material, such as a perovskite material. In some cases, block 130 can include a membrane separation process. In some cases, the membrane separation process can be a slurry-based process, for example involving a slurry including the beneficiated coal. In some cases, a membrane separation process can include, or be carried out in, a protonic ceramic membrane reactor. In some cases, these products can be substantially similar to the products produced by a liquefaction process, but may not use the amount of heat or pressure that a liquefaction process can require. Thus, in some cases, processing beneficiated coal with one or more membranes can produce substantially similar products to a liquefaction process but can require substantially less energy to do so. In some embodiments, the one or more membranes can comprise various pore sizes, chemical properties, physical properties, or electrical properties to isolate desirable compounds and/or produce desirable compounds from the beneficiated coal.

In some embodiments, block 130 can comprise processing the beneficiated coal using an electric arc process. For example, block 130 can include heating the beneficiated coal in an electric arc furnace. In some cases, such a process can include heating the beneficiated coal in the electric arc furnace to one or more temperatures between about 1800° C. and about 2000° C. for a duration. In some cases, the beneficiated coal can be heated at about atmospheric pressure. In some cases, such an electric arc heating process can produce one or more gases, such as acetylene. In some cases, this acetylene can be subjected to further processing to form one or more advanced carbon materials or precursors for forming the same. For example, acetylene produced during an electric arc process can be subjected to further processing to form one or more of polyvinyl chloride, polyvinyl alcohol, and butanediol. In some cases, the acetylene or any gases formed during the electric arc process can be utilized in further processing of the coal as described herein.

In some embodiments, one or more additives can be added to the beneficiated coal at block 140. In some embodiments, one or more other gases or liquids can be used during the processes of block 140. For example, hydrogen containing gases can be added to or used during a coal liquefaction process. In some cases, natural gases, $CO_2$, or petroleum products can be used as additives during block 130. In some embodiments, the one or more additives can include materials or compounds that are produced during blocks 120 and/or 130, or that can be produced by or captured during previous iterations of process 100.

At block 140, pitch, char, gases, and/or coal liquid are produced via the processing facility. The skilled artisan will appreciated that block 140 can represent the result of blocks 120 and 140, rather than a separate action or process step. While the blocks 110-150 together define the method 100, the method can include additional steps as described herein.

In some embodiments, pitch can be produced via the processing facility at block 140. As used herein, pitch, also known as coal pitch, coal tar, or coal tar pitch, can refer to a mixture of one or more typically viscoelastic polymers as will be well understood by the skilled artisan. In some embodiments, the pitch produced at block 140 can be a direct result of processing the beneficiated coal at step 130. The pitch produced at block 140 can comprise one or more high molecular weight polymers. In some embodiments, the pitch can have a melting point of greater than about 650° F. In some embodiments, the pitch can have a melting point that is high enough that the pitch can be used in a carbon fiber spinning process, for example as described herein, without the need for a plasticizer. In some cases, the pitch can be an isotropic pitch. In some cases, this isotropic pitch can be subjected to further processing at block 150, such as heating in an inert atmosphere as described herein, to form or produce mesophase pitch. As used herein, the term mesophase pitch can be refer to any pitch that is greater than about 40% mesophase. In some cases, however, the term mesophase pitch can be used to refer to pitch that includes any amount of pitch in a mesophase state.

In some embodiments, the pitch can comprise aromatic hydrocarbons, for example polycyclic aromatic hydrocarbons. In some cases, the pitch can comprise at least about 50 wt. % polycyclic aromatic hydrocarbons, at least about 60 wt. %, 70 wt. %, 80 wt. %, 90 wt. %, 95 wt. %, or 99 wt. % or greater of polycyclic aromatic hydrocarbons. In some embodiments, the pitch can be relatively free of impurities, such as water, non-carbon atoms including sulfur or nitrogen, or material such as coal ash or char. In some cases, the pitch can comprise less than about 0.2 wt. % water, less than about 0.1 wt. %, less than about 0.05 wt. %, or less than about 0.01 wt. % water or lower. In some cases, the pitch can comprise less than about 0.1 wt. % ash or other solid material, less than about 0.05 wt. % ash or solid material, or less than about 0.01 wt. % ash or solid material. In some cases, the pitch can have a flash point greater than about 230° F., greater than about 250° F., or greater than about 300° F. In some cases, the pitch can have an API gravity of less than about 4, less than about 3, or less than about 2, or less. In some embodiments, the pitch can have a hydrogen to carbon (H:C) ratio of less than about 1, less than about 0.8, less than about 0.5, less than about 0.2, less than about 0.1, or lower. In some embodiments, the pitch can be an isotropic pitch. In some embodiments, the pitch produced by the method 100 is not coke pitch. That is, in some cases, the pitch produced at block 140 is not produced from coke or a coke based material. In some embodiments, coke is not produced at any point during the method 100.

In some embodiments, char can be produced via the processing facility at block 140. As used herein, char, also known as ash, can refer to any solid material which remains after gases, liquids, and/or pitch have been removed from raw coal. For example, in some embodiments, char can be produced during the beneficiation of raw coal at block 120. In some embodiments, char can be produced by the processing of block 130. In some embodiments, char can be produced as a result of blocks 120 and 130.

In some embodiments, char can comprise a solid high surface area carbonaceous material. In some cases, char can have a relatively low H:C ratio, for example lower than the H:C ratio of pitch produced at block 140. In some cases, char can have an H:C ratio of from about 0.05 to about 0.65. In some cases, char can additionally comprise at least some pitch material, which can be referred to herein as intrinsic binder impregnation. In some cases, any residual pitch or other gaseous or liquid materials can be removed from the char prior to any subsequent processing of the char.

In some embodiments, any char produced at block 140 can be subjected to further processing, for example to produce an advanced carbon material such as activated carbon. In some cases, char can be carbonized or heated, for example in a rotary kiln, as part of this further processing. In some cases the char can then be activated, for example via a physical activation process or a chemical activation process. In some cases, physical activation can comprise heating the char in an atmosphere comprising argon and/or nitrogen, or heating the char in an oxidizing atmosphere. In some cases, chemical activation can comprise impregnating the char with one or more chemicals, such as an acid, a base, or a salt. In some cases, chemical activation can further comprise carbonizing or heating the impregnated char to activate it. In some cases, chemical activation can require lower temperatures and less energy than physical activation. Further, in some cases, chemical byproducts produced by the method 100 can be utilized during the chemical activation process.

In some embodiments, one or more liquids can be produced via the processing facility at block 140. These liquids are referred to collectively as coal liquid extracts herein, and can refer to any material that is extracted or produced from raw coal and is liquid at or near normal temperature and pressure (about 68° F. and 1 atmosphere of pressure). For example, in some embodiments, coal liquid extracts can be produced during the beneficiation of raw coal at block 120. In some embodiments, coal liquid extracts can be produced by the processing of block 130. In some embodiments, coal liquid extracts can be produced as a result of blocks 120 and 130.

In some embodiments, one or more gases can be produced via the processing facility at block 140 and can be captured for later use or reuse. In some embodiments, these gases can be produced during the beneficiation of raw coal at block 120. In some embodiments, gases can be produced by the processing of block 130. In some embodiments, gases can be produced as a result of blocks 120 and 130. In some embodiments, the captured gas or gases can comprise hydrogen and/or carbon. In some cases, the captured gas or gases can comprise sulfur. Such gases can include, for example, $H_2$, $CO_2$, CO, $CH_4$, $C_2H_4$, $C_3H_6$, and/or other hydrocarbon gases. As described herein, in some cases, the captured gases produced by the method 100 can themselves be used as precursors to form advanced carbon materials. In some cases, the processing of block 130 is not carried out in an atmosphere that includes $H_2$.

In some embodiments, coal liquid extracts can comprise one or more liquid hydrocarbons. For example, coal liquid extracts can comprise one or more of benzene, toluene, alkanes or paraffins, alkenes, or other saturated or unsaturated hydrocarbons. In some embodiments, coal liquid extracts produced at block 140 can be subjected to further processing, for example to refine or isolate specific liquids, or to convert coal liquid extracts to other liquid compounds. For example, the coal liquid extracts can be subjected to a process to convert one or more of the coal liquid extracts to benzene and/or paraxylenes. In some cases, the coal liquid extracts can be subjected to processing to produce advanced carbon material, such as resins or polymers. In some cases, the coal liquid extracts can be processed to form polyurethane resins, cyanate ester resins, epoxy resins, methacrylate resins, polyester resins, and others.

Pitch, char, gases, and coal liquid extracts are all described as being produced at block 140, however in some embodiments, one or more of these products can be produced at separate times or separate processing steps from any other product. In some embodiments, one or more of pitch, char, and coal liquid extracts can be produced together by a process step and can need to be separated before any further processing of each individual product can occur. For example, pitch and coal liquid extracts can be simultaneously produced as a result of block 130 and can need to be separated from one another, by any process now know or which can be developed in the future, before further processing of either pitch or coal liquid extracts occurs. Accordingly, the method 100 can comprise a further step of separating one or more of the pitch, char, and coal liquid extracts from each other prior to block 150.

At block 150, the pitch produced at block 140 can be treated via the processing facility to produced one or more advanced carbon materials described herein. In some embodiments, the pitch of block 140 is not subjected to further processing or refinement to alter the chemical composition of the pitch before being treated to form an advanced carbon material. However, in some other embodiments, the pitch can be subjected to one or more processes which can alter the chemical composition of the pitch prior to block 150. For example, impurities can be removed from the pitch prior to block 150. In some cases, the pitch can be subjected to one or more processes to produce mesophase pitch or otherwise alter the composition or properties of the pitch In some embodiments, block 150 can comprise spinning the pitch produced at block 140 to form carbon fibers. In some cases, the pitch can be heated to a desired temperature during the spinning process, for example to about 650° F. In some cases, block 150 can comprise any process known in the art or developed in the future to convert pitch to carbon fibers, or carbon filament. For example, block 150 can comprise drawing, spinning, and heating the pitch to produce carbon fibers. In some cases, block 150 can comprise spinning filaments of the pitch, heating the pitch in air to a first temperature, and then heating the spun pitch in an inert atmosphere to a second, higher temperature to form carbon filament. In some cases, a plasticizer can be added to the pitch to aid in spinning the pitch, however in some other embodiments, plasticizer may not be added before spinning the pitch. In some embodiments, block 150 can comprise treating the pitch to produce one or more of any of the advanced carbon materials described herein.

Spinning—spinning the fiber from mesophase pitch then thermoset the fiber by heating in an O containing atmos, then carbonizing by heating in an inert atmos to remove hydrogen and other volatiles and produce all-carbon fiber In some embodiments, block 150 can comprise processing the pitch to form synthetic graphite. In some cases, the synthetic graphite can be subjected to further processing to form synthetic graphene. For example, in some embodiments block 150 can comprise treating the pitch, for example by exposure to heat, elevated pressure, and/or one or more catalysts to form synthetic graphite. As used herein, the term synthetic graphite is used to refer to any graphite material produced from a precursor material, for example any graphite material that does not occur naturally in the earth. In some embodiments, block 150 can further comprise treating or processing the synthetic graphite to form synthetic graphene. As used herein, synthetic graphene refers to any graphene material produced or derived from synthetically formed graphite. For example, block 150 can comprise subjecting the synthetic graphite to mechanical exfoliation to produce synthetic graphene.

In some embodiments, the method 100 can further comprise capturing at least some of the gases, liquids, or other volatile compounds which can be produced as a result of the method, 100, including blocks 110-150. In some embodiments at least 50%, at least 75%, at least 90%, 95%, or 99% of any gaseous or volatile byproducts of the method 100 can be captured. In some cases, some or all of these captured or retained gaseous or volatile byproducts can then be used in the steps of the method 100. For example, $CO_2$ gas can be produced by one or more of the steps of method 100, which can be captured and subsequently used in any of the steps of method 100. In some cases, the capture and reuse of byproducts can improve the efficiency and/or lower the cost of the method 100.

According to some embodiments, an advanced carbon material can be produced from coal by a method or process including:
  providing coal to a processing facility;
  beneficiating the coal via the processing facility to remove a desired amount or range of amounts of water, metals, volatile compounds, and other impurities from the coal;
  processing at least some of the beneficiated coal via the processing facility;
  producing pitch, char, gases, and/or coal liquid extract; and
  treating one or more of the pitch, char, gases, and/or coal liquid extract via the processing facility to produce one or more advanced carbon materials.

Figure 2:
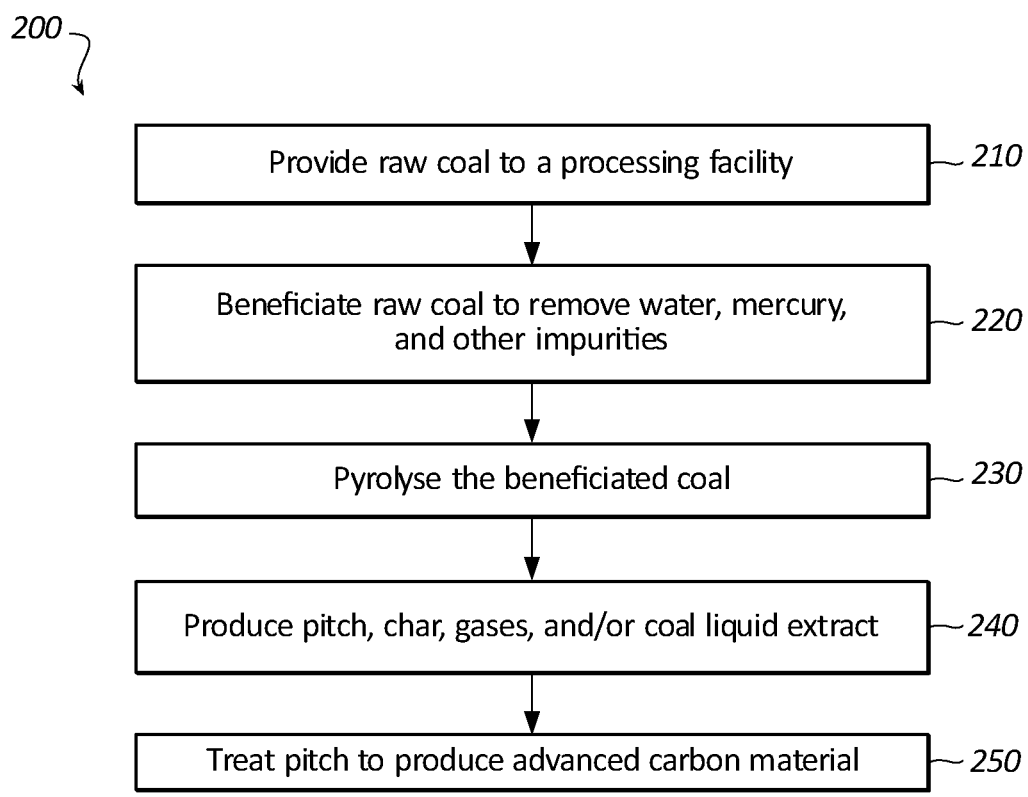
FIG. 2 illustrates a process flow diagram of an example of a method of producing advanced carbon material from coal including a pyrolysis process in accordance with the present disclosure.

According to some embodiments, and as illustrated in FIG. 2, an advanced carbon material can be produced from coal by a method or process 200 including:
  providing coal to a processing facility at block 210;
  beneficiating the coal via the processing facility at block 220 to remove a desired amount or range of amounts of water, metals, and other impurities from the coal;
  pyrolyzing at least some of the beneficiated coal via the processing facility at block 230;
  producing pitch, char, gases, and/or coal liquid extract at block 240; and
  treating at least one of the pitch, char, gases, and coal liquid extract via the processing facility at block 250 to produce the advanced carbon material. Although the method 200 describes a process flow for producing a single type of advanced carbon material via a processing facility, the method 200 can be used to produce more than one type of advanced carbon material via the processing facility. For example, the method 200 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 200. Further, while producing pitch, char, gases, and/or coal liquid extract is described as a separate block 240, the pitch, char, gases, and/or coal liquid extract can be produced as a result of blocks 220 and/or 230 any may not be a separate process step in and of itself.

Figure 3:
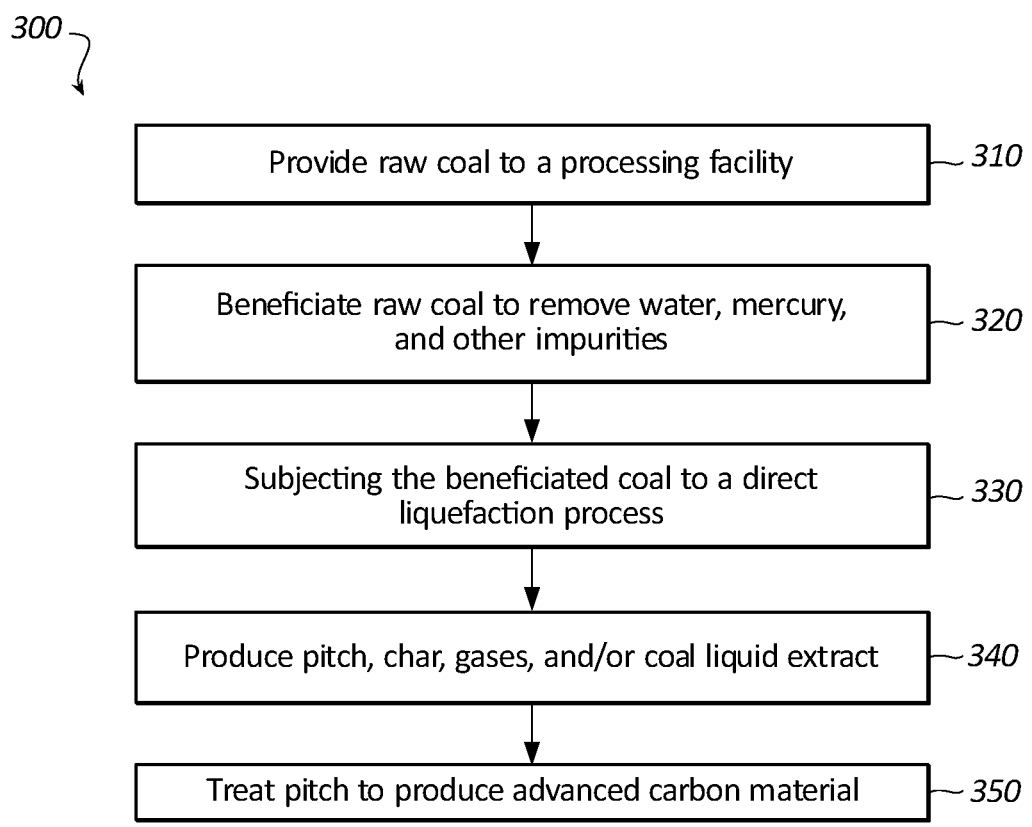
FIG. 3 illustrates a process flow diagram of an example of a method of producing advanced carbon material from coal including a direct liquefaction process in accordance with the present disclosure.

According to some embodiments, and as illustrated in FIG. 3, an advanced carbon material can be produced from coal by a method or process 300 including:
  providing coal to a processing facility at block 310;
  beneficiating the coal via the processing facility at block 320 to remove a desired amount or range of amounts of water, metals, and other impurities from the coal;
  subjecting at least some of the beneficiated coal to a direct liquefaction process via the processing facility at block 330;
  producing pitch, char, gases, and/or coal liquid extract at block 340; and
  treating at least one of the pitch, char, gases, and coal liquid extract via the processing facility at block 350 to produce the advanced carbon material.

Figure 4:
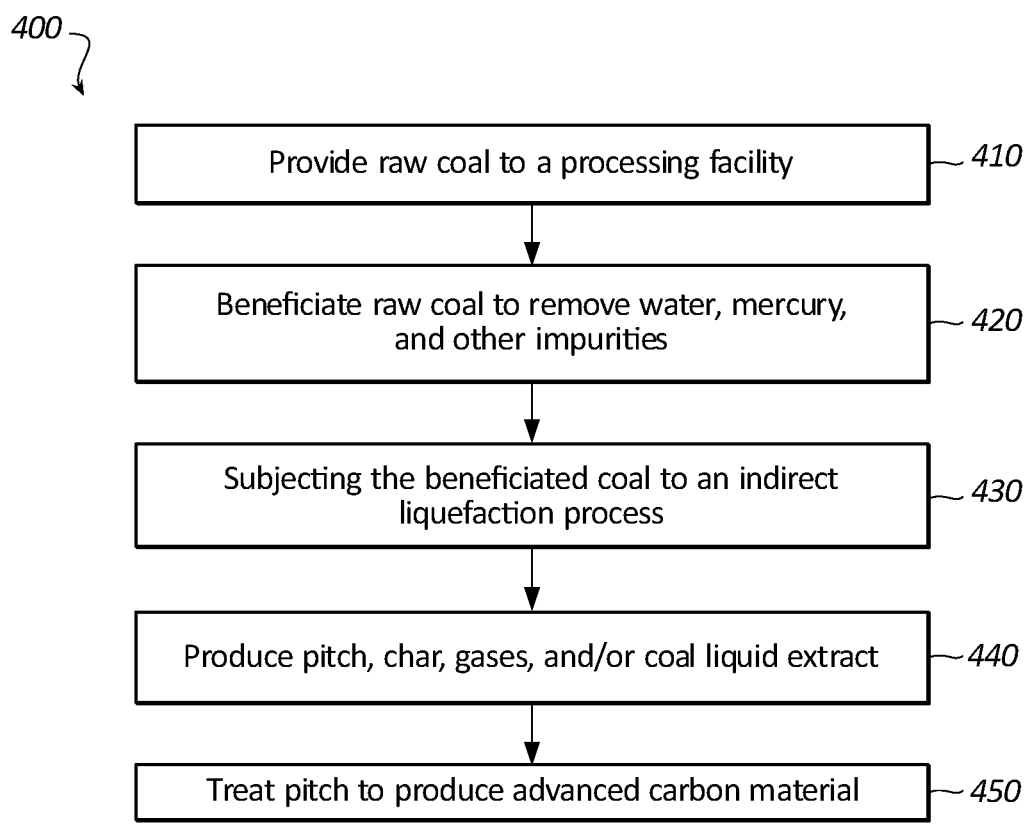
FIG. 4 illustrates a process flow diagram of an example of a method of producing advanced carbon material from coal including an indirect liquefaction process in accordance with the present disclosure.

Although the method 300 describes a process flow for producing a single type of advanced carbon material via a processing facility, the method 300 can be used to produce more than one type of advanced carbon material via the processing facility. For example, the method 300 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 300. Further, while producing pitch, char, gases, and/or coal liquid extract is described as a separate block 340, the pitch, char, gases, and/or coal liquid extract can be produced as a result of blocks 320 and/or 330 any may not be a separate process step in and of itself. According to some embodiments, and as illustrated in FIG. 4, an advanced carbon material can be produced from coal by a method or process 400 including:
  providing coal to a processing facility at block 410;
  beneficiating the coal via the processing facility at block 420 to remove a desired amount or range of amounts of water, metals, and other impurities from the coal;
  subjecting at least some of the beneficiated coal to an indirect liquefaction process via the processing facility at block 430;
  producing pitch, char, gases, and/or coal liquid extract at block 440; and
  treating at least one of the pitch, char, gases, and coal liquid extract via the processing facility at block 450 to produce the advanced carbon material.

Although the method 400 describes a process flow for producing a single type of advanced carbon material via a processing facility, the method 400 can be used to produce more than one type of advanced carbon material via the processing facility. For example, the method 400 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 400. Further, while producing pitch, char, gases, and/or coal liquid extract is described as a separate block 440, the pitch, char, gases, and/or coal liquid extract can be produced as a result of blocks 420 and/or 430 and may not be a separate process step in and of itself.

Figure 5:
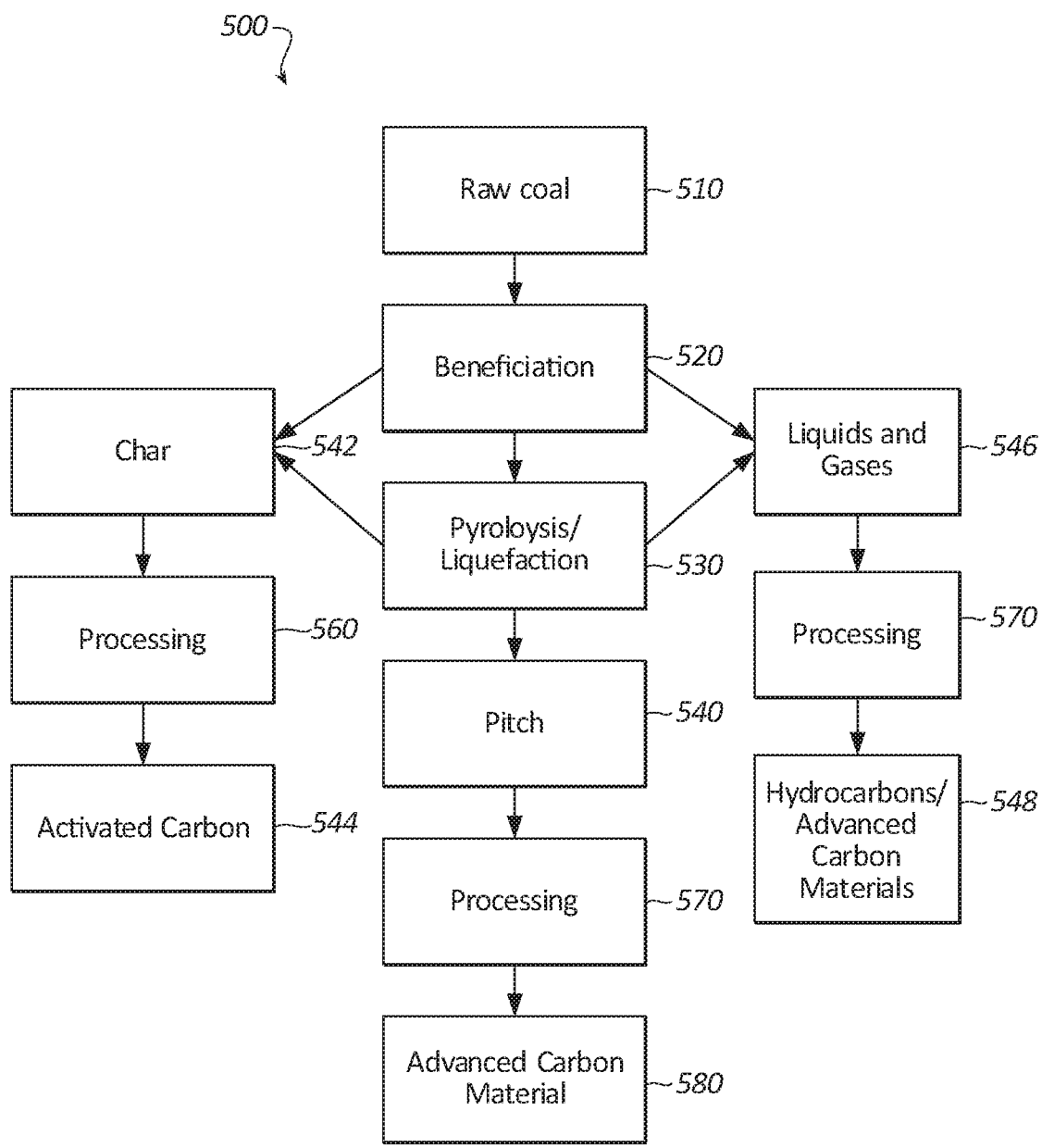
FIG. 5 illustrates a material flow diagram of an example of a method of producing advanced carbon materials from coal in accordance with the present disclosure.

FIG. 5 illustrates a material flow diagram of an example of a method 500 of producing one or more advanced carbon materials from coal in accordance with the present disclosure. At block 510, raw coal is provided to a processing facility, for example by a mining process, such as high wall mining. The raw coal can then be subjected to a beneficiation process to remove a desired amount of or range of amounts water, metals, volatile matter, and other impurities as described herein at block 520. In some cases, the beneficiation process can produce byproducts, such as char (block 542) and gases and/or coal liquid extracts (546), in addition to the upgraded coal. The upgraded coal can be subjected to a pyrolysis, direct liquefaction, or indirect liquefaction process at block 530 and as described herein to produce pitch (block 540). Again, in some cases, the pyrolysis or liquefaction process of block 540 can produce byproducts, such as char (block 542) and coal liquid extracts and gases (block 546). In some cases, the char 542 can be processed or treated at block 560 to produce an advanced carbon material, for example activated carbon (block 544) as described herein. In some cases, the coal liquid extract 546 can be processed or treated at block 570 to produce hydrocarbons, such as benzene and paraxylenes and/or other advanced carbon materials (block 548) as described herein. At block 550, the pitch can be processed or treated to produce one or more advanced carbon materials (block 580), such as carbon fibers or graphene as described herein.

In some embodiments, the method 500 can be entirely carried out at a single processing facility. However, in some other cases, one or more blocks can be carried out at different processing facilities and/or different locations. For example, char 542 or coal liquid extract 546 can be transported to a second location where blocks 560 and 570 can be carried out.

Although the processes described herein relate to the production of advanced carbon materials from coal, in some embodiments these processes can be utilized to produce silicon products, such as silicone resins. For example, in some embodiments, sand or other raw materials comprising silicon can be used in the processes and methods described herein to produce one or more silicone resins.

Figure 6:
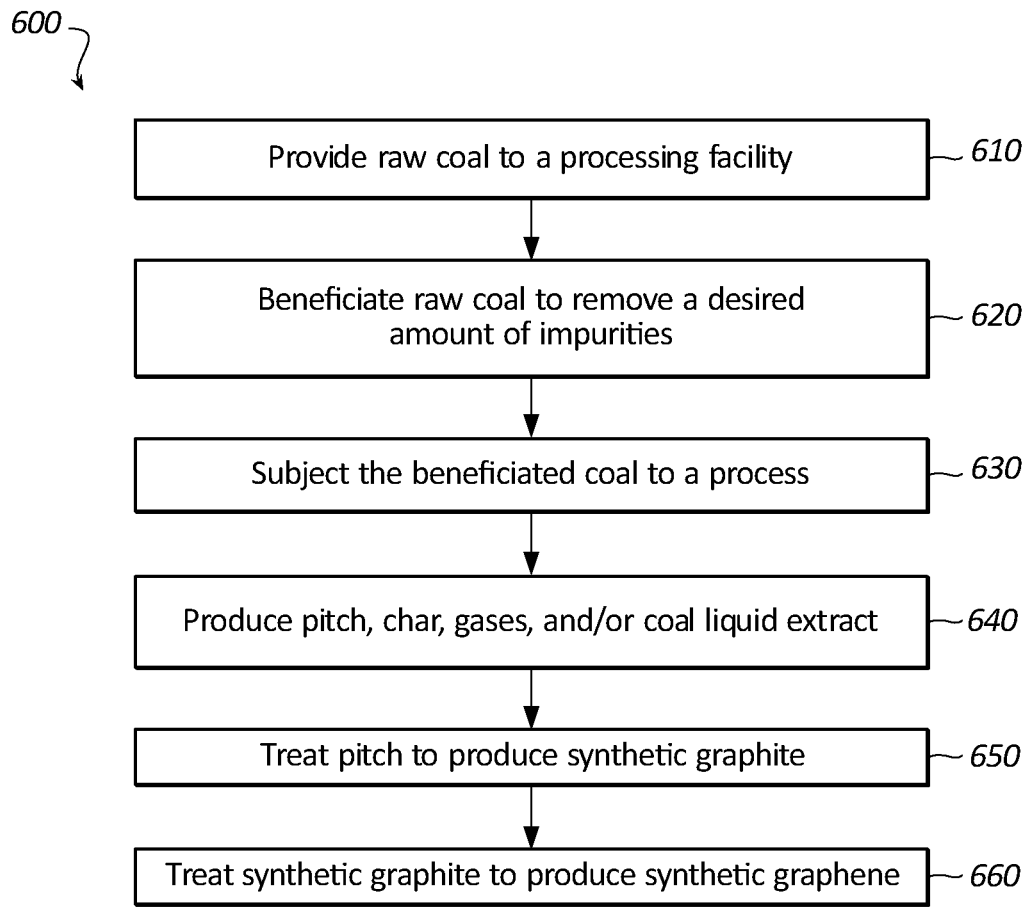
FIG. 6 illustrates a process flow diagram of an example of a method of producing graphene from coal in accordance with the present disclosure.

According to some embodiments, and as illustrated in FIG. 6, synthetic graphene can be produced from coal by a method or process 600 including:

providing coal to a processing facility at block 610;

beneficiating the coal via the processing facility at block 620 to remove a desired amount or range of amounts of water, mercury, cadmium, selenium, other heavy metals, and/or other impurities from the coal;

processing at least some of the beneficiated coal via the processing facility at block 630;

producing pitch, char, gases, and/or coal liquid extract at block 640; and treating at least one of the pitch, char, gases, and coal liquid extract via the processing facility at block 650 to produce synthetic graphite;

treating the synthetic graphite via the processing facility at block 660 to produce the synthetic graphene.

As described herein, a desired amount or range of amounts of one or more impurities can remain in the beneficiated coal at block 620 and can thereby be incorporated into the synthetic graphene produced at block 660 in order to adjust the chemical, electrical, and/or physical properties of the synthetic graphene. For example, a desired amount or range of amounts of boron and/or nitrogen can remain in the beneficiated coal at block 620 to, for example, create a bandgap in the synthetic graphene.

Figure 7:
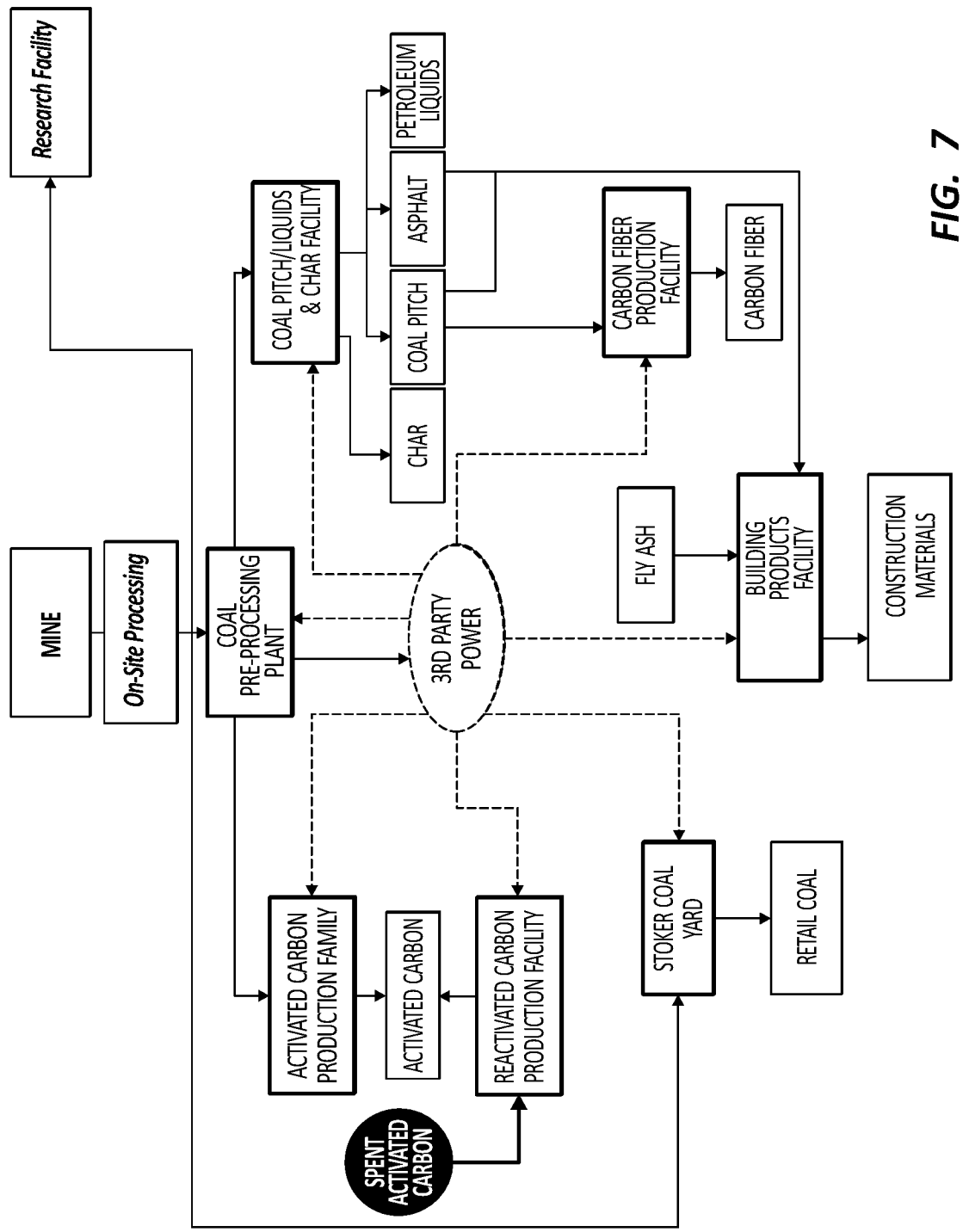
FIG. 7 illustrates a diagram of energy and material flows for the production advanced carbon materials in accordance with the present disclosure.

FIG. 7 is a diagram illustrating the flow of energy and coal in a processing facility for the production of one or more advanced carbon materials as described herein and according to some embodiments. As can be seen in FIG. 7, and as described herein, raw coal from a mine, such as the Brook Mine in Sheridan, Wyo., can be processed to form one or more advanced carbon materials, such as carbon fiber, construction materials, and/or activated carbon.

Figure 8:
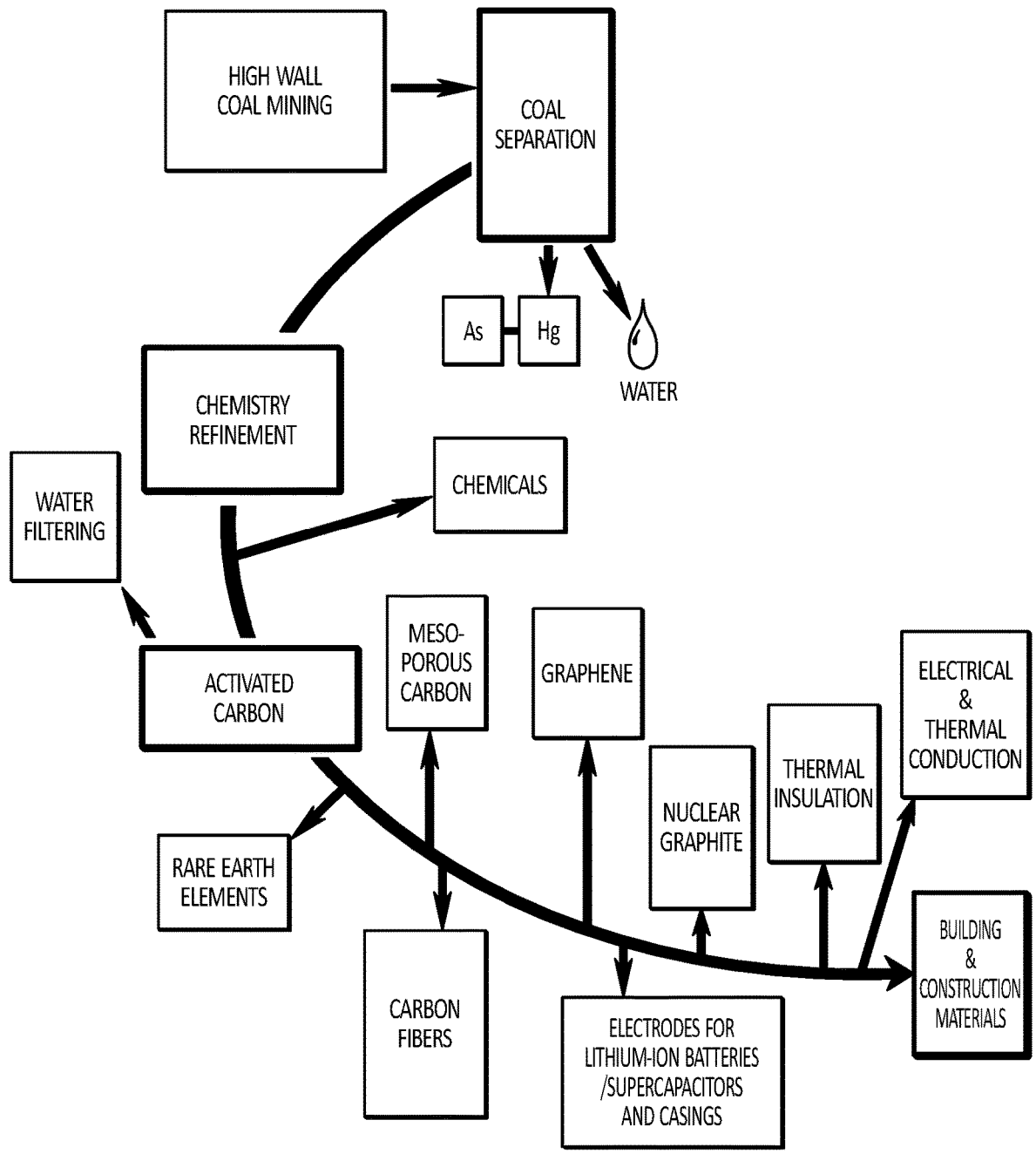
FIG. 8 illustrates a process flow diagram of the production of advanced carbon materials from raw coal in accordance with the present disclosure.

FIG. 8 is a diagram illustrating the process flow of raw coal, for example from a high wall coal mine, as it is processed according to the embodiments described herein to form various advanced carbon materials, such as activated carbon, graphene, materials for use in batteries, and building and construction materials. As illustrated, and according to some embodiments, processing of the coal can produce advanced carbon materials which can themselves be subjected to further processing to form other advanced carbon materials. Further, in some embodiments, the byproducts from the production of advanced carbon materials can themselves be subjected to further processing to produce other advanced carbon materials as described herein.

Figure 9:
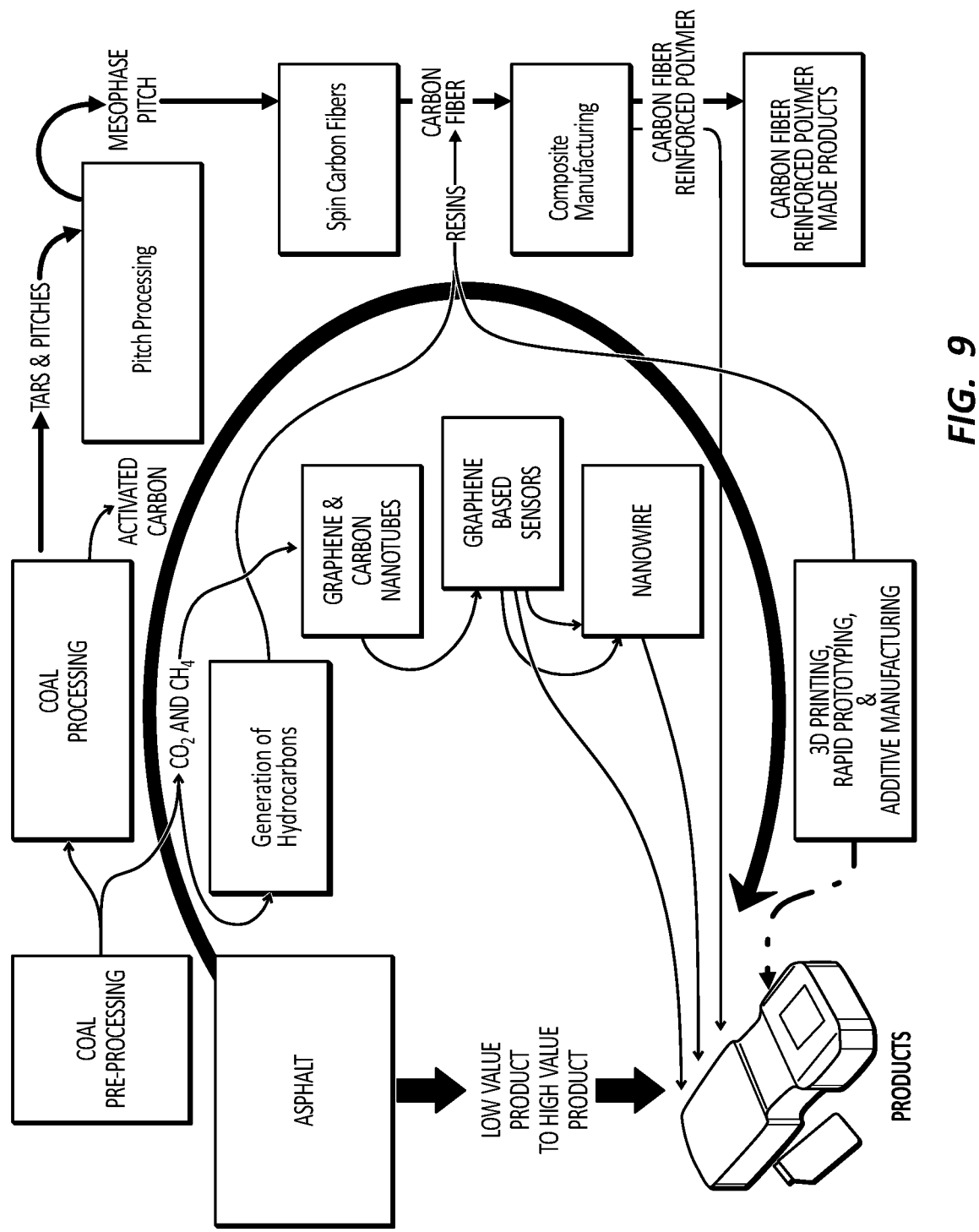
FIG. 9 illustrates a process flow diagram of the production of products including advanced carbon materials from raw coal in accordance with the present disclosure.

FIG. 9 is a diagram illustrating the process flow of raw coal to various advanced carbon material according to the processes described herein. FIG. 9 further illustrates how, according to some embodiments, the advanced carbon material produced according to the processes described herein can be utilized as one or more components in high-value finished products, such as automotive grade CFRP, or graphene based biosensors.

Advanced Carbon Materials

The methods and processes described herein can be used to produce one or more advanced carbon materials from coal. As used herein, the term advanced carbon materials can refer to one or more materials comprising carbon. In some embodiments, an advanced carbon material can be an allotrope of carbon and can consist essentially of carbon. In some embodiments, an advanced carbon material can be a resin, polymer, or other hydrocarbon material.

In some cases, an advanced carbon material can comprise primarily carbon atoms. In some embodiments, an advanced carbon material can comprise carbon fibers, carbon foams, activated carbon, and/or pyrolyzed carbon. In some embodiments, an advanced carbon material can comprise one or more allotropes of carbon, for example any allotropes of carbon that are known in the art or that can be developed in the future. In some cases, an advanced carbon material can comprise single-walled carbon nanotubes, multi-walled carbon nanotubes, carbon megatubes, carbon nanoribbons, carbon nanobuds, graphite, graphene, graphite nano-platelets, quantum dots, and fullerenes, such as buckminsterfullerene and multi-cored fullerenes.

In some cases, an advanced carbon material can comprise elements in addition to carbon and can be, for example, a resin, polymer, or other hydrocarbon material. For example, an advanced carbon material can comprise polyurethane resins, cyanate ester resins, epoxy resins, methacrylate resins, polyester resins, and others. In some cases, an advanced carbon material can comprise thermoset or thermoplastic polymers. In some cases, an advanced carbon material can comprise a polyester, vinyl ester, or nylon polymer.

In some cases, an advanced carbon material can comprise a biologically useful material or biopolymer. That is, in some cases an advanced carbon material can comprise a material including carbon that is used in biological systems or organisms, that is biocompatible, or that can typically be produced by a biological organism. For example, in some embodiments an advanced carbon material can be a protein, amino acid, nucleic acid, collagen, chitosan, sugar, or other biological material. In some cases, an advanced carbon material can comprise a porous material, such as a membrane, for use in a biological and/or chemical process. For example, an advanced carbon material can comprise perforated graphene.

In some embodiments where the advanced carbon material can comprise carbon fibers, the carbon fibers can have different or improved physical properties as compared to carbon fibers formed by conventional processes, for example by spinning polyacrylonitrile (PAN). In some cases, carbon fibers produced by the processes described herein can have a higher degree of molecular orientation along the fiber axis than carbon fibers produced from PAN. In some cases, carbon fibers produced by the processes described herein can have a higher elastic modulus than carbon fibers produced from PAN. In some cases, carbon fibers produced by the processes described herein can have a higher thermal and electrical conductivity than carbon fibers produced from PAN. However, in some embodiments, an advanced carbon material can comprise PAN, and thus carbon fibers can be produced from PAN that is formed from coal according to the processes described herein.

Applications

The advanced carbon material or materials produced via the methods and processes described herein can be used in a wide variety of applications. In some cases, the advanced carbon materials produced via the processing facility described herein can be subjected to further processing to produce objects, devices, and other products from the advanced carbon materials. In other embodiments, the advanced carbon materials can be distributed to other production facilities for use. Importantly, in some embodiments, the processes described herein can produce two or more types of advanced carbon materials which can be combined at the processing facility into further products.

In some cases, and as described herein, a first amount of pitch can be treated to produce a first advanced carbon material, and a second amount of pitch can be treated to produce a second, different advanced carbon material. In some cases, the first and second advanced carbon materials can be combined to form a new material and/or produce. For example, the first advanced carbon material can comprise carbon fibers and the second advanced carbon can comprise a polymer or resin. The first and second advanced carbon materials can then be combined via the processing facility to produce carbon fiber reinforced polymer by any process known in the art or that can be developed in the future. In some cases, the carbon fiber reinforced polymer can be formed into a desired structure, for example a part or product as specified by a customer. In some embodiments, an advanced carbon material can be produced via the processes described herein and can be combined with one or more other materials via the processing facility to produce a composite material having a desired form. For example, the advanced carbon material can comprise carbon nanotubes. These carbon nanotubes can then be metalized via the processing facility to produce a carbon nanotube metal matrix composite. In some cases, the carbon nanotube metal matrix composite can comprise a bulk material, however in some other cases the carbon nanotube metal matrix composite can be formed in a desired shape. In some cases, a carbon nanotube metal matrix composite can be formed by any processes known in the art or that can be developed in the future, such as via powder metallurgy processes, electrochemical processes, melt processes, and others.

In some cases where the advanced carbon material includes activated carbon, the activated carbon materials can be functionalized and tuned as desired. In some cases, any of the advanced carbon materials described herein can include activated carbon and/or can be functionalized, such as PAN, resins, carbon fibers, and the like. For example, in some cases an advanced carbon material produced according to the methods described herein can be functionalized to adsorb one or more predetermined materials, elements, and/or substances from water, the atmosphere, or other mediums as desired. In some cases, advanced carbon material produced according to the methods described herein can adsorb one or more types of rare earth elements produced by coal processing plants, such as the processing facilities described herein. In some cases, advanced carbon material produced according to the methods described herein can adsorb one or more valuable predetermined elements or compounds from sea water. In some cases, advanced carbon material produced according to the methods described herein can adsorb $CO_2$ from the ambient atmosphere.

In some embodiments where an advanced carbon material can comprise a resin, the resin can be subjected to further processing via the processing facility to produce a polymer part or product. In some cases, the resin can be used in a three dimensional printing process to form polymer structures such as meshes, hollow objects, solid objects, or other products. In some embodiments, a resin produced by the processes described herein can be used in a continuous liquid interface production (CLIP) process as developed by Carbon3D, Inc., to produce a wide variety of polymer objects via the processing facility. Carbon3D, Inc. uses a number of different resins to provide end products with selectable properties via the CLIP process. In some embodiments, the methods and processes described herein can be used to produce any of the resins used in the CLIP process, for example, polyurethane resins, ester resins, epoxy resins, and others. Accordingly, the processing facility can comprise one or more CLIP printers, such as the M2 Printer developed by Carbon3D, Inc., which can print polymer parts derived directly from coal as described herein. For example, in some embodiments, advanced carbon materials produced from coal by the processes described herein can be used in the CLIP process via the processing facility to print dental products which are customized to an individual patient's anatomy. While custom dental products are provided as an example, almost any form of three-dimensional object can be produced via the processes described herein.

For example, in some embodiments where an advanced carbon material comprises one or more resins for use in 3D printing, such resins can be used to 3D print products specific to the needs of each customer. For example, such 3D printed products can have dimensions corresponding to the custom measurements of each customer. In some examples, products 3D printed using resins produced via the processes described herein can include custom helmets, pads, or other protective clothing for use in sporting activities and/or combat. In some embodiments, one or more body parts of a user or customer can be scanned and the dimensions thereof can be incorporated into the custom design of the 3D printed product. In some cases, custom 3D printed products using resins produced via the processes described herein can include custom fitted horse shoes and/or saddles.

In some embodiments, the advanced carbon material resins used in a 3D printing process can be modified on site by a user in order to achieve the desired chemical or mechanical properties of the final 3D printed product. For example, a first resin produced from coal by the processes described herein can have a first physical property in a final cured state, such as a first young's modulus. Where a user desires to adjust this property, they can be direct to add a predetermined amount of a second resin or other advanced carbon material produced from coal to the first resin, where the second resin and amount thereof can be selected based on the nature of the adjustment to the first physical property of the first resin produced from coal. For example, where a user desires a higher young's modulus, they can be directed to add a predetermined amount of a second resin produced from coal in order to raise the young's modulus of the first resin. In some cases, this addition can be carried out automatically based on the desired cured material properties of the 3D printed object.

In some embodiments, the material properties of a 3D printed objected can be varied throughout the volume of the object by utilizing two or more resins produced form coal according to the processes described herein that are UV activatable, where each of the two or more resins has different material properties when cured and each is activated by a different wavelength of UV light. For example, in some embodiments a first resin produced from coal having a first material property, such as a first stiffness, can be activated by a first wavelength of UV light. A second resin produced from coal having a second, different material property, such as a second stiffness, can be activated by a second, different wavelength of UV light. The resins can be activated by UV light to form the product as it is being 3D printed, and the wavelength of the UV light can be adjusted to vary the material properties of the product as it is being printed. For example, UV light having a wavelength corresponding to the activation wavelength of the first resign can be used for those parts of the product where the material properties of the first resin are desired. The wavelength can then be varied or changed to the activation wavelength of the second resin so that the material properties of the printed object vary from the properties of the first resin to the properties of the second.

In some embodiments, a first advanced carbon material produced by the processes described herein can be used in a subsequent such process to produce a second, different advanced carbon material. For example, the first advanced carbon material can comprise molecular graphene membranes. The molecular graphene membranes can then be used in the processes described herein to chemically separate products of pyrolysis or liquefaction processes to produce resins. In some cases, this form of chemical separation via graphene membranes can be more thermally efficient than other separation processes that are typically employed. These resins in turn can be used in the CLIP process, for example to print a mesh.

In some embodiments where an advanced carbon material comprises graphene, the graphene can be subjected to further treatment via the processing facility to form, for example, a graphene sensor. These graphene sensors can be used as disposable chips for detecting diseases via a hand-held device. The graphene sensor can be able to immediately detect diseases, such as Lyme disease or the zika virus from a patient's blood, urine, saliva, or other bodily fluids or biological material, thereby eliminating any need to store blood samples for transportation to a lab. Further, the processes described herein can also be used to print the body of the hand-held device, and/or a consumable or attachment, such as a microfluidic chamber, for example via the CLIP process.

In some embodiments, advanced carbon materials produced by the processes described herein can be used in a wide variety of other applications. For example, the advanced carbon material can comprise a carbon foam which can be used as an electrode in a lithium ion battery. In some cases, the advanced carbon material can comprise activated carbon that can be used in an atmospheric $CO_2$ recapture process. In some cases, the atmospheric $CO_2$ recapture process can be carried out via the processing facility and captured $CO_2$ can be used in the processes described herein.

In some embodiments, advanced carbon materials, such as graphene, formed according to the processes described herein can be used to produce solar panels. In some cases these solar panels can have greater efficiencies than other conventionally produced solar panels. In some embodiments, advanced carbon materials formed according to the processes described herein can be used as precursors in electrospinning processes. For example, advanced carbon materials can be used to electrospin scaffolds or other structures having micron level resolution. In some cases the advanced carbon materials used in electrospinning can be biomaterials produced from coal according to the processes described herein. In some embodiments advanced carbon materials can be used to produce gels, for example medical grade gels such as hydrogels or silicone gels.

In some embodiments, one or more advanced carbon materials produced from coal according to the processes described herein can be used as automotive grade materials in the production of cars, trucks, or other automobiles. For example, carbon fibers, resins, and/or CFRPs can be used as automotive frames, structural components, body panels, engine blocks, and/or other components. In some cases, the components can be 3D printed and can be custom designed according to a user's preferences.

In some embodiments, one or more advanced carbon materials produced from coal according to the processes described herein can be used to form products for use in chemical or biological processes, such chromatography columns, membranes, and filters. In some cases, chromatography columns, membranes, and/or filters can be 3D printed from one or more advanced carbon materials produced from coal according to the processes described herein. In some cases, the chromatography columns, membranes, and/or filters can be used to isolate or remove antibodies, bacteria, parasites, and/or heavy metals from various solutions.

In some embodiments, one or more advanced carbon materials produced from coal according to the processes described herein can be used to form circuit boards. For example, a carbon foam produced from coal as described herein can be 3D printed to form a circuit board. In some cases a carbon foam circuit board can have superior electrical and thermal properties to typical printed circuit boards. In some embodiments, one or more advanced carbon materials produced from coal according to the processes described herein can be synthetic graphene and can be used in a variety of electronic applications, for example in forming quantum dots and in computer chips. In some cases, graphene can be used to produce biosensors that can be capable of isolating and/or identifying any number of biologically active molecules or substances, such as disease biomarkers or viruses.

In some embodiments, one or more advanced carbon materials produced from coal according to the processes described herein can include composite materials, such as metals or concrete including carbon fibers, graphene, or other advanced carbon materials. In some examples, metal including one or more advanced carbon materials such as graphene, carbon fibers, or carbon nanotubes can be 3D printed. In some examples, carbon fiber or CFRPs produced from coal as described herein can be used as rebar in concrete or can be used as other construction materials.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

We claim:

1. A method of producing an advanced carbon material, comprising:
    providing an amount of coal to a processing facility;
    beneficiating the amount of coal at the processing facility to remove impurities therefrom;
    processing the beneficiated amount of coal at the processing facility to produce an amount of pitch from at least some of the amount of coal; and
    treating at least some of the amount of pitch at the processing facility to produce the advanced carbon material.

2. The method of claim 1, wherein providing coal to a processing facility comprises extracting coal from a coal mine.

3. The method of claim 2, wherein extracting coal from the coal mine comprises a high wall coal mining process.

4. The method of claim 1, wherein providing coal to a processing facility further comprises transporting the coal extracted from the coal mine to the processing facility.

5. The method of claim 1, wherein the amount of coal is an amount of raw coal.

6. The method of claim 1, wherein beneficiating the amount of coal comprises heating the amount of coal to a first temperature for a first duration; and heating the amount of coal to a second, higher temperature for a second duration.

7. The method of claim 1, wherein beneficiating the amount of coal removes at least 85% of mercury from the amount of coal.

8. The method of claim 1, wherein beneficiating the amount of coal produces a beneficiated amount of coal having less than about 5 wt. % of water.

9. The method of claim 1, wherein beneficiating the amount of coal removes at least 50% of volatile matter from the amount of coal.

10. The method of claim 1, wherein processing the beneficiated amount of coal at the processing facility to produce an amount of pitch from at least some of the amount of coal comprises subjecting the beneficiated amount of coal to at least one of a pyrolysis process, a direct liquefaction process, an indirect liquefaction process, a membrane separation process, and an electric arc process.

11. The method of claim 1, wherein the pitch comprises at least one of isotropic pitch and mesophase pitch.

12. The method of claim 1, wherein treating at least some of the amount of pitch at the processing facility to form the advanced carbon material comprises spinning at least some of the amount of pitch to produce the advanced carbon material.

13. The method of claim 1, wherein the advanced carbon material comprises one or more of carbon fibers, carbon nanotubes, graphite, graphene, graphite nano-platelets, fullerenes, pyrolytic carbon, carbon foams, and resins.

14. The method of claim 1, wherein treating at least some of the amount of pitch at the processing facility comprises treating a first amount of pitch to form a first advanced carbon material and treating a second amount of pitch to form a second advanced carbon material.

15. The method of claim 11, wherein the first advanced carbon material comprises carbon fibers and the second advanced carbon material comprises a polymer.

16. A method of producing carbon fibers from coal at a processing facility, comprising:
    providing coal to the processing facility;
    beneficiating the coal to remove impurities therefrom;
    subjecting the beneficiated coal to one or more of a pyrolysis process, a direct liquefaction process, an indirect liquefaction process, a membrane separation process, and an electric arc process to thereby produce a pitch; and
    treating the pitch to produce one or more advanced carbon materials.

17. The method of claim 16, wherein the one or more advanced carbon materials include one or more of resins, pitch, carbon fibers, or graphene.

* * * * *